United States Patent
Gilmour et al.

(10) Patent No.: US 7,118,741 B1
(45) Date of Patent: Oct. 10, 2006

(54) TRANSEPITHELIAL TRANSPORT OF MOLECULAR SPECIES

(75) Inventors: Jacqueline Elizabeth Mary Gilmour, Dursley (GB); David Joseph Unsworth, Bristol (GB)

(73) Assignee: The National Blood Authority, Mertfordshire (GB)

( * ) Notice: Subject to any disclaimer, the term of this patent is extended or adjusted under 35 U.S.C. 154(b) by 0 days.

(21) Appl. No.: 08/952,707

(22) PCT Filed: May 13, 1996

(86) PCT No.: PCT/GB96/01152

§ 371 (c)(1),
(2), (4) Date: Apr. 9, 1998

(87) PCT Pub. No.: WO96/35719

PCT Pub. Date: Nov. 14, 1996

(30) Foreign Application Priority Data

May 12, 1995 (GB) .................................. 9509620

(51) Int. Cl.
*A61K 39/395* (2006.01)

(52) U.S. Cl. ................. 424/130.1; 424/132.1; 424/136.1; 424/141.1; 424/152.1; 424/156.1; 530/391.1; 530/391.5; 530/391.7

(58) Field of Classification Search ............. 424/130.1, 424/132.1, 136.1, 141.1, 152.1, 156.1; 530/391.1, 530/39.15, 391.7
See application file for complete search history.

(56) References Cited

FOREIGN PATENT DOCUMENTS

| EP | 0255249 B1 | 4/1995 |
|---|---|---|
| WO | WO 89/01343 | 2/1989 |
| WO | WO 90/08779 A1 | 8/1990 |

OTHER PUBLICATIONS

Kaetzel et al (PNAS, 88:8796-8800), 1991.*
Kaetzel et al (J. Immunol., 152:72-76), 1994.*
Fahey et al (Clin. Exp. Immunol., 88:1-5), 1992.*
Fox (B90/Technology, 12:128), 1994.*
Adorini et al (Immunol. Today, 11:383-386), 1990.*
Klausner (Biotechnology, 4:103-104), 1985.*
Blanco Quiros et al (Eur. J. Pediatr, 1994, 153:103-106).*
Taber's Cyclopedic Medical Dictionary, (FA. Davis Company, Philadelphia, 1989, p. 1807).*
Johnstone and Thorpe (Immunochemistry in Practice, Blackwell Scientific Publications, Oxford, 1987, pp 49-50).*
Kraehenbuhl, J.P., et al., "Receptor-Mediated Transepithelial Transport of Secretory Antibodies and Engineering of Mucosal Antibodies", Chem. Abstracts, vol. 110, No. 3, Jan. 16, 1989, Abstract No. 19368n, p. 145.
Kraehenbuhl, J.P., et al., "Receptor-Mediated Transepithelial Transport of Secretory Antibodies and Engineering of Mucosal Antibodies", Adv. Exp. Med. Biol., vol. 216B, 1989, pp. 1053-1060.

* cited by examiner

*Primary Examiner*—Susan Ungar

(74) *Attorney, Agent, or Firm*—Townsend and Townsend and Crew LLP

(57) ABSTRACT

There is disclosed a synthetic cross-linker protein capable of binding a molecule or macromolecular species to a transcytosis receptor for transport of the molecule or macromolecule species across a mucous membrane, said cross-linker protein comprising a first binding region capable of binding selectively to a site on the said molecule or macromolecular species to be transported and a second binding region capable of binding selectively to a site on said receptor, wherein the first binding region is the antigen-binding site of a first antibody molecule having specificity for an antigenic site on said molecule or macromolecular species to be transported and the second binding region is the antigen-binding site of a second antibody molecule which has specificity for an antigenic site on the said transcytosis receptor.

8 Claims, No Drawings

… (US 7,118,741 B1)

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:1:

CAGCTGCAGC TGCAGCAGTC TGG                                            23

(2) INFORMATION FOR SEQ ID NO:2:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

CAGGTCAACC TGCAGGAGTC TGG                                            23

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

GAGGTGCAGC TGCAGGAGTC TGG                                            23

(2) INFORMATION FOR SEQ ID NO:4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

CAGGTGCAGC TGCAGGAGTC GGG                                            23

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

CAGGTACAGC TGCAGCAGTC AGG                                            23

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

CTTGGTGGRT GCTGAKGAGA CGCTGACC                                       28

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

GACATCCAGC TGACCCAGTC TCC                                            23

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

GATATTCAGC TGACTCAGTC TCC                                            23

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

GAAATTCAGC TGACGCAGTC TCC                                            23

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

AGACTCTCCC CTGTTGAAGC TCTT                                         24

(2) INFORMATION FOR SEQ ID NO:11:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

AACCAGCCAT GGCCTCTGAG CTGACTCAGG ACCC                        34

(2) INFORMATION FOR SEQ ID NO:12:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

AACCAGCCAT GGCCCAGTCT GTGTTGACGC AGCC                                  34

(2) INFORMATION FOR SEQ ID NO:13:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

AACCAGCCAT GGCCTCCTAT GTGCTGACTC AGCC                                  34

(2) INFORMATION FOR SEQ ID NO:14:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

TGAAGATTCT GTAGGGGCCA CTGTCTT                                          27

(2) INFORMATION FOR SEQ ID NO:15:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

TCAGGAGGCG GAGGCTCTGG AGGAGGTGGC AGTGAGGTGC AGCTGCAGGA GTCTGG          56

(2) INFORMATION FOR SEQ ID NO:16:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

TCAGGAGGCG GAGGCTCTGG AGGAGGTGGC AGTCAGGTGC AGCTGCAGCA GTCTGG          56

(2) INFORMATION FOR SEQ ID NO:17:

(i) SEQUENCE CHARACTERISTICS:
        (A) LENGTH: 56 base pairs
        (B) TYPE: nucleic acid
        (C) STRANDEDNESS: single (D) TOPOLOGY: linear (ii) MOLECULE TYPE: DNA (xi) SEQUENCE DESCRIPTION: SEQ ID NO:17:

TCAGGAGGCG GAGGCTCTGG AGGAGGTGGC AGTCAGCTGC AGCTGCAGGA GTCGGG           56

(2) INFORMATION FOR SEQ ID NO:18:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

TCAGGAGGCG GAGGCTCTGG AGGAGGTGGC AGTCAGGTAC AGCTGCAGCA GTCAGG           56

(2) INFORMATION FOR SEQ ID NO:19:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

TCAGGAGGCG GAGGCTCTGG AGGAGGTGGC AGTCAGGTCA ACCTGCAGGA GTCTGG           56

(2) INFORMATION FOR SEQ ID NO:20:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

CGGACTAGTC TTGGTGGAGG CTGATGAGAC GGCGAC                                 36

(2) INFORMATION FOR SEQ ID NO:21:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

CGGACTAGTC TTGGTGGGGG CTGAGGAGAC GGCGAC                                 36

(2) INFORMATION FOR SEQ ID NO:22:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

GCATTAGGCC TCGAGGGCCT CGAWATTCAG CTGACKCAG             39

(2) INFORMATION FOR SEQ ID NO:23:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

GCATTAGGCC TCGAGGGCCT CGACATCCAG CTGACCCAG             39

(2) INFORMATION FOR SEQ ID NO:24:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

GAGCCTCCGC CTCCTGATCC GCCACCTCCG AAGACAGATG GTGCAGCCAC AGT             53

(2) INFORMATION FOR SEQ ID NO:25:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

GCATTAGGCC TCGAGGGCCT CCCAGCCATG GCC             33

(2) INFORMATION FOR SEQ ID NO:26:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

AGAGCCTCCG CCTCCTGATC CGCCACCTCC CGAGGGGGCA GCCTT             45

(2) INFORMATION FOR SEQ ID NO:27:

(i) SEQUENCE CHARACTERISTICS:
        (A) LENGTH: 15 amino acids
        (B) TYPE: amino acid
        (C) STRANDEDNESS:
        (D) TOPOLOGY: linear -continued (ii) MOLECULE TYPE: peptide (xi) SEQUENCE DESCRIPTION: SEQ ID NO:27:

```
Gly Gly Gly Gly Ser Gly Gly Gly Gly Ser Gly Gly Gly Gly Ser
1               5                  10                  15
```

TRANSEPITHELIAL TRANSPORT OF MOLECULAR SPECIES

This invention relates to the transepithelial transport of molecular species, and is particularly concerned with a synthetic bi-functional or cross-linker protein which is capable of binding to a molecular species, particularly a macromolecule such as an antibody, which is not normally capable of being secreted across a membrane, the cross-linker additionally having a binding region capable of binding the thus-formed macromolecule/cross-linker complex to transcytosis receptors present in epithelial cells (such as those seen in the mucous membranes (mucosa)).

BACKGROUND

Epithelial cells are cells which line a cavity, or cover a surface and can form a selective barrier to the exchange of molecules between the lumen of an organ and an underlying tissue. In many types of epithelia, the extracytoplasmic leaflet of apposing cells is fused together by tight junctions, which preclude the paracellular diffusion of macromolecules.

The principal mechanism of transport of macromolecules across cells with tight junctions is via vesicular carriers, in a process which is known as transcytosis. Normally, the molecule that is to be transcytosed first binds to a receptor. The receptor-ligand complex then enters the cell by endocytosis to form a vesicle. Transcytotic vesicles are subsequently formed which are delivered to the opposite cell surface where they fuse with the plasma membrane and release their contents into secretions. Transcytosis may occur in either direction, from the apical to basolateral surface or from the basolateral to apical cell surface.

IgA is an immunoglobulin which is found in a wide variety of mucosal secretions, including gastrointestinal and respiratory secretions, and also bile. After formation, secretory IgA (sIgA) is taken up by an overlying epithelial cell, transported across the cell and released into external secretions where the IgA forms the first specific immunologic defence against infections. The receptor that transports the sIgA (and also the IgM) is known as the polymeric immunoglobulin receptor (pIgR). In the normal route of secretion, sIgA interacts with the pIgR on the surface of epithelial cells. The antibody is internalised and transported through the cell within a vesicle to the apical surface. On release from the cell the pIgR is proteolytically cleaved, releasing a polypeptide known as the secretory component (SC) which remains attached to the antibody. The receptor is specific for polymeric immunoglobulins, such as IgA and IgM, but IgG will not interact with the receptor.

Immunoglobulin G (IgG) is a distinct immunoglobulin from IgA and IgM. IgG immunoglobulins have a molecular weight of about 160,000 and constitute over 85% of the immunoglobulins in the sera of most normal and hyperimmune individuals. The molecule consists of two heavy chains having a molecular weight each of about 50,000 and two light chains having a molecular weight each of about 25,000. The proteins of the IgG class may be differentiated into four sub-classes, IgG-1 to IgG-4, each of which has a distinct heavy chain. IgG preparations from human blood products are used in the clinical management of a wide variety of diseases, and is used in particular for patients with immunodeficiency. The IgG preparation is normally delivered intravenously, but also may be delivered intramuscularly or by subcutaneous injection. Whilst IgG preparations are effective in many circumstances, because IgG is not capable of being secreted across mucosal membranes, it is therefore less able to function as part of the first immunologic defence against infection, in, for instance, the gastrointestinal and respiratory tracts.

SUMMARY OF THE INVENTION

Broadly stated, the invention relates to novel composite proteins having dual binding affinity (a) for a transcytosis receptor in a mucous membrane and (b) for a molecule or macromolecular species, the binding affinity being provided by the antigen-binding sites of appropriate antibody molecules.

DETAILED DESCRIPTION OF THE INVENTION

In accordance with a first aspect of the present invention, there is provided a synthetic cross-linker protein capable of binding a molecule or macromolecular species to a transcytosis receptor for transport of the molecule or macromolecular species across a mucous membrane, said cross-linker protein comprising a first binding region capable of binding selectively to a site on the said molecule or macromolecular species to be transported and a second binding region capable of binding selectively to a site on said receptor, wherein the first binding region is the antigen-binding site of a first antibody molecule having specificity for an antigenic site on said said molecule or macromolecular species to be transported and the second binding region is the antigen-binding site of a second antibody molecule which has specificity for an antigenic site on the transcytosis receptor.

The synthetic cross-linker protein according to the invention may comprise the whole or a functional fragment of the first antibody molecule covalently linked to the whole or a functional fragment of the second antibody molecule in such a way that the respective antigen-binding sites are capable of binding their respective target antigens. Thus, for example, the synthetic cross-linker protein may comprise the whole of the first antibody molecule covalently linked to the whole of the second antibody molecule, or may comprise a fragment of the first antibody molecule covalently linked to a fragment of the second antibody molecule.

It is preferred that the second binding region of the cross-linker protein is capable of binding selectively to a site on the polymeric immunoglobulin receptor (pIgR), for example a site on the secretory component (SC) portion of pIgR.

The molecule to be transported is preferably a macromolecule, such as a protein. For convenience, we refer in the remainder of this specification mainly to "macromolecules", which are the preferred molecules to be modified in accordance with the invention. This should not be construed as limiting the present invention to the transepithelial transport of macromolecules. It should be understood that the term "macromolecule" embraces associations or aggregates of smaller macromolecules, for instance proteins which are made up of two or more sub-units which may be covalently linked or which may be held together by non-covalent forces. Using the invention, it is also possible to modify other molecules, such as drugs or nucleic acids, so that they are capable of undergoing transcytosis.

The synthetic cross-linker protein of the present invention represents a powerful tool for achieving the delivery of macromolecules from one side of a membrane to the other side of the membrane, when the macromolecule is not normally capable of being secreted across that membrane under physiological conditions.

Specific cross-linker proteins in accordance with the present invention can be designed to bind to a wide range of different molecules, preferably macromolecules such as proteins. The cross-linker of the present invention is particularly useful in making possible transcytosis of antibodies, such as IgG, employing a transcytosis receptor such as the polymeric immunoglobulin receptor (pIgR).

In use, the cross-linker protein is contacted with a source of the molecule, preferably macromolecule, to be transported so as to form a complex between the cross-linker protein and the macromolecule, and the macromolecule/cross-linker complex is then introduced into a patient, normally via the intravenous route. The macromolecule/cross-linker complex is capable of being secreted across the epithelia as a consequence of the binding specificity of the cross-linker protein with a transcytosis receptor, such as polymeric immunoglobulin receptor, in the epithelia. Alternatively, the cross-linker protein may be infused so that it selectively binds to a target molecule in vivo, resulting in specific excretion of that target molecule, such as a protein, by a secretory route across the epithelia by virtue of binding to a transcytosis receptor, such as the polymeric immunoglobulin receptor. The macromolecule/cross-linker complex is capable of being secreted across a mucosal membrane by virtue of its inherent specificity for the transcytosis receptor.

The present invention is particularly useful where the macromolecule to be transported is an immunoglobulin, in which case the first binding region of the cross-linker protein should have binding specificity for a site on the said immunoglobulin.

In one preferred aspect, the macromolecular species to be transported is IgG and the first binding region has binding specificity for a site on the constant region of said IgG. Thus, in accordance with a second aspect of the invention, there is provided a synthetic cross-linker protein capable of binding IgG to a transcytosis receptor for transport thereof across a mucous membrane, said cross-linker protein comprising the whole or a functional fragment of a first antibody molecule, including at least its antigen-binding site, covalently linked to the whole or a functional fragment of a second antibody molecule, including at least its antigen-binding site, wherein the antigen-binding site of the first antibody molecule is capable of binding selectively to an antigenic site on the constant region of the heavy chain of IgG and the antigen-binding site of the second antibody molecule is capable of binding selectively to an antigenic site on said transcytosis receptor. Preferably, the antigen-binding site of the second antibody molecule is capable of binding selectively to a site on the polymeric immunoglobulin receptor (pIgR), for example a site on the secretory component (SC) portion of pIgR.

Also provided is a pharmaceutical composition, preferably in an injectable form, for use in the treatment of a immuno-deficient patient, comprising donor IgG and an amount of synthetic cross-linker protein in accordance with the second aspect of the invention sufficient to bind at least a proportion of said donor IgG for delivery of IgG to an internal organ defined by a mucous membrane of the patient.

This preferred aspect of the invention provides an improved treatment for immuno-deficient patients undergoing donor IgG therapy. Specifically, the pharmaceutical composition, preferably in an injectable form, makes it possible to deliver donor IgG having broad specificity to the mucosal membranes which are normally isolated from such treatment. The pharmaceutical composition is prepared simply by mixing the cross-linker protein with donor IgG. Because all of the donor IgG will have the same common region in its structure, the cross-linker protein will bind IgG having the necessary broad specificity. Typically, the pharmaceutical composition will comprise a balance of free IgG and IgG bound to the cross-linker protein. The relative amounts of free and bound IgG will depend upon the amount of the cross-linker protein in the composition. The actual relative amounts will depend upon the patient undergoing therapy, but typically will be such that about 10–20% of the IgG is bound to the cross-linker protein. The total IgG used is normally about 0.2–0.4 g/kg body weight per month. The pharmaceutical composition is preferably injected intravenously or subcutaneously.

In another preferred aspect, the macromolecular species to be transported is an autoantibody, such as an IgG autoantibody and the first binding region is capable of binding selectively to a site on the variable region of said autoantibody. Thus, in accordance with a third aspect of the invention, there is provided a synthetic cross-linker protein capable of binding an autoantibody, preferably an IgG autoantibody, to a transcytosis receptor for transport thereof across a mucous membrane, said cross-linker protein comprising the whole or a functional fragment of a first antibody molecule, including at least its antigen-binding site, covalently linked to the whole or a functional fragment of a second antibody molecule, including at least its antigen-binding site, wherein the antigen-binding site of the first antibody molecule is capable of binding selectively to an antigenic site on the variable region of said autoantibody and the antigen-binding site of the second antibody molecule is capable of binding selectively to an antigenic site on said transcytosis receptor. Preferably, the antigen-binding site of the second antibody molecule is capable of binding selectively to a site on the polymeric immunoglobulin receptor (pIgR), for example a site on the secretory component (SC) portion of pIgR.

Also provided is a pharmaceutical composition, preferably in an injectable form, for use in the treatment of a patient suffering from an auto-immune disease which is caused by an autoantibody, comprising an amount of synthetic cross-linker protein in accordance with the third aspect of the invention as defined above effective to bind said autoantibody.

This aspect of the invention provides a therapy for certain auto-immune diseases which are caused by an autoantibody, for example Systemi Lupus Erythematosus (SLE). Treatment of the patient with a pharmaceutical composition in which the cross-linker protein has affinity for the specific autoantibody will enable them to be selectively removed and secreted from the body via the gut bile duct, which has a mucosal membrane including transcytosis receptors. The cross-linker protein must be chosen to bind selectively to the autoantibodies responsible for the auto-immune disease, and not other normal IgG present in the patient's circulation. This can be done by targeting the variable region of the IgG to be removed, which will be highly specific to autoantibodies.

Suitable techniques for designing cross-linker proteins having the desired specificity are discussed below.

Typically, the cross-linker protein is prepared by identifying a first antibody or functional antibody fragment capable of binding to the molecule or macromolecule concerned, and identifying a second antibody or functional antibody fragment which is capable of binding to a site of a transcytosis receptor contained in the mucous membrane across which the molecule is to be transported, and then combining the first antibody or functional antibody fragment and second antibody or functional antibody fragment to form a single cross-linker protein in which the binding specificities of the "parent" antibodies are retained.

When the first and second antibodies (or antibody fragments) have been identified, they are combined to form a single cross-linker protein which retains the binding specificity of each of the original antibodies. This combining of the first and second antibodies or antibody fragments may be achieved by simple chemical joining of the two molecules by, for example, a disulphide link. Alternatively, and preferred, is to ligate DNA coding for each of the antibodies or antibody fragments to form a single DNA molecule which can then be expressed in a host to produce a single protein containing the binding regions from the polypeptides previously identified.

It is highly preferred that the cross-linker protein is constructed from first and second functional antibody fragments each containing at least a substantial part of the variable region(s) derived from one or preferably both of the light and heavy chains. Such antibody fragments are preferred because techniques now exist for the skilled person to express in a host cell functional antibody fragments which are capable of binding specifically to antigenic sites on any desired macromolecule. Examples of antibody fragments prepared by these techniques are the so-called $F_v$ and $F_{ab}$ fragments. The $F_v$ fragment is a heterodimer of only the variable domains of the heavy and the light chain. Normally, the two chains of the $F_v$ fragment are linked covalently by, for example, a peptide linker to form what is known as a single-chain $F_v$. The use of single-chain $F_v$s is particularly preferred in the present invention. The $F_{ab}$ fragment is similar to the $F_v$ fragment, but additionally contains the constant domain of the light chain and the first constant domain of the heavy chain. The chains of the $F_{ab}$ fragment are not normally covalently linked but instead are held together by non-covalent forces. More details concerning the preparation and characterisation of antibody fragments may be found in the article entitled "Antibody Engineering: Advances from the use of *Escherichia Coli* Expression Systems", by Andreas Plückthun, *Biotechnology*, Vol. 9, p545–551 (June 1991).

The identification of suitable antibody fragments, preferably single-chain $F_v$s, may be achieved by a technique in which the functional antibody fragment is displayed on the surface of a bacteriophage where it may be directly selected with antigen. This technique is described in detail in an article entitled "Phage Antibodies: will new 'colicloncal' antibodies replace monoclonal antibodies", by David J. Chiswell et al, *Tibtech*, Vol. 10, p80–84 (March 1992). In this technique, cellular mRNA is isolated and cDNA prepared. Heavy and light chain variable regions of immunoglobulin molecules are amplified by PCR using specific primers. The variable regions of the heavy and light chains are joined by a flexible peptide linker by PCR splicing. The PCR products are then cut with suitable restriction endonuclease(s) and ligated into a phagemid vector which has been similarly cut. The phagemid vector is then transformed into a suitable host vector such as *E. coli* and, using helper phage, phagemid particles displaying the fusion protein are produced.

A phagemid library containing phagemid particles displaying a range of antibody fragments can be prepared and this is then screened to identify the antibody fragment which displays affinity for (a) the target molecule (preferably a macromolecule) and (b) the relevant transcytosis receptor. Thus, it follows that such targets should possess a viable antigenic site. Once the phagemid particles displaying the desired antibody fragment have been identified, the DNA from each is purified and the coding sequences ligated with a sequence coding for a short peptide linker. The construct can then be ligated into a suitable vector, transformed into a host cell and the bivalent antibody fragment isolated by known procedures.

In a preferred aspect of the present invention, a cross-linker protein is synthesised which has affinity for the constant region of IgG and affinity for the polymeric immunoglobulin receptor. This cross-linker protein is preferably a bivalent antibody fragment constructed from two single chain $F_v$ fragments which have been identified by the techniques described above as having binding affinity for the constant region of IgG and for the polymeric immunoglobulin receptor.

According to another aspect of the invention, there is provided a pharmaceutical composition comprising a macromolecule bound to a cross-linker protein according to the first aspect of this invention. Preferably, the macromolecule is IgG, and the cross-linker molecule comprises a region having affinity for the polymeric immunoglobulin receptor, as well as affinity for the constant region of IgG. The IgG may be polyclonal or monoclonal. Preferably it is polyclonal and is separated from blood products.

The cross-linker protein of the present invention may be used to deliver other macromolecules, such as drugs, across a mucous membrane.

The cross-linker protein may also be added to a patient to target specific macromolecules present in the patient which it is desired to remove or absorb, for example pathological immunoglobulins, or anti-nuclear and other auto antibodies. The cross-linker protein is constructed to bind to specific, characteristic regions of the macromolecule to be removed. Once bound to the cross-linker molecule, the macromolecule/cross-linker complex is capable of being secreted via the bile duct system.

The following example illustrates the invention.

EXAMPLE

In this example, a synthetic cross-linker protein is constructed which has affinity both for the constant region of IgG (a non-secretory immunoglobulin) and the polymeric immunoglobulin receptor which is the main transcytosis receptor in the mucous membrane.

Construction of single-chain $F_v$ (sc$F_v$)

Human peripheral blood lymphocytes were isolated, mRNA prepared from the cells and first strand cDNA was produced (Clackson T., D. Gussow & P. T. Jones (1992) in PCR: A practical Approach, Ed. McPherson M. J. P. Quirke & G. R. Taylor, IRL Press). Heavy and light chain variable regions of immunoglobulin molecules were amplified by PCR using the primers detailed in Table 1. The variable regions of the heavy and light chains were joined randomly by a flexible peptide linker ((Glycine$_4$ Serine)$_3$) (SEQ ID NO:27) by PCR splicing using the linkers detailed in Table 2. The PCR products were then cut with Sfil and Spel and ligated into a phagemid vector (pAC36) which had been similarly cut. The phagemid vector was transformed into *E. coli* and, using helper phage, phagemid particles displaying the fusion protein were produced.

Screening of scFv

Supernatant from *E. coli* transformed with the recombinant phagemid vector was collected. It contained phagemid particles displaying a range of sc$F_v$s: this supernatant is known as a phagemid library. This library was screened for scFv displaying affinity for IgG constant region and for polymeric Ig receptor (pIgR) by panning, as described, for example by Nissim, A, H. R. Hoogenboom, I. M. Tomlinson, G. Flynn, C. Midgley, D. Lane & G. Winter (1994) EMBO J. 13 692–698. Briefly, the target molecule was coated onto plastic tubes and the phagemid library added. After incubation the unbound phagemids were washed off and bound phagemid eluted. This procedure was repeated with the bound phagemid with increasing stringency until scF$_v$ of the desired specificities were isolated.

Construction of Bivalent F$_v$

Once the two phagemid displaying scF$_v$ of the desired specificity were isolated, the DNA from each was purified. The scF$_v$ coding sequences were removed and joined with a sequence coding for a short peptide linker. The construct was then ligated into an *E. coli* expression vector. The bivalent F$_v$ produced by the *E. coli* was isolated from the supernatant using standard protein purification techniques.

Assessment of Efficiency of Transport

The ability to transfer the IgG across epithelial cells can be measured using a technique described in Mazanec M. B., J. G. Nedrud, C. S. Kaetzel & M. E. Lamm (1993) Immunology Today 14 430–434. The bivalent F$_v$ is ═mixed with human monoclonal antibody specific for RhD positive blood cells. The mixture is then placed in contact with a layer of cultured epithelial cells which express pIgR. The epithelial cells were grown on a permeable membrane which divides the culture vessel and only by interaction with the pIgR can the IgG be transported into the apical compartment of the culture vessel. As two monoclonal antibodies of different isotypes specific for RhD positive red cells, the levels of IgG1 and IgG3 transported can be measured by agglutination assays and by ELISA.

TABLE 1

PCR Primers for the Amplification of Variable Regions of the Heavy and Light Chains Heavy—Sense 1. 5' CAG CTG CAG CTG CAG CAG TCT GG  (SEQ ID NO. 1)

2. 5' CAG GTC AAC CTG CAG GAG TCT GG  (SEQ ID NO. 2)

3. 5' GAG GTG CAG CTG CAG GAG TCT GG  (SEQ ID NO. 3)

4. 5' CAG GTG CAG CTG CAG GAG TCG GG  (SEQ ID NO. 4)

5. 5' CAG GTA CAG CTG CAG CAG TCA GG  (SEQ ID NO. 5)

Heavy—Anti-sense

5' CTT GGT GG(A/G) TGC TGA (G/T)GA GAC GCT GAC C  (SEQ ID NO. 6)

Light (Kappa)—Sense 1. 5' GAC ATC CAG CTG ACC CAG TCT CC  (SEQ ID NO. 7)

2. 5' GAT ATT CAG CTG ACT CAG TCT CC  (SEQ ID NO. 8)

3. 5' GAA ATT CAG CTG ACG CAG TCT CC  (SEQ ID NO. 9)

Light (Kappa)—Anti-sense

5' AGA CTC TCC CCT GTT GAA GCT CTT  (SEQ ID NO. 10)

Light (Lambda)—Sense 1. 5' AAC CAG CCA TGG CCT CTG AGC TGA CTC AGG ACC C  (SEQ ID NO. 11)

2. 5' AAC CAG CCA TGG CCC AGT CTG TGT TGA CGC AGC C  (SEQ ID NO. 12)

3. 5' AAC CAG CCA TGG CCT CCT ATG TGC TGA CTC AGC C  (SEQ ID NO. 13)

Light (Lambda)—Anti-sense

5' TGA AGA TTC TGT AGG GGC CAC TGT CTT  (SEQ ID NO. 14)

TABLE 2

PCR Primers for Linking Heavy and Light Variable Regions

Heavy—Sense 1. 5' TCA GGA GGC GGA GGC TCT GGA GGA GGT GGC AGT GAG  (SEQ ID NO. 15)
   GTG CAG CTG CAG GAG TCT GG 2. 5' TCA GGA GGC GGA GGC TCT GGA GGA GGT GGC AGT CAG  (SEQ ID NO. 16)
   GTG CAG CTG CAG CAG TCT GG 3. 5' TCA GGA GGC GGA GGC TCT GGA GGA GGT GGC AGT CAG  (SEQ ID NO. 17)
   CTG CAG CTG CAG GAG TCG GG 4. 5' TCA GGA GGC GGA GGC TCT GGA GGA GGT GGC AGT CAG  (SEQ ID NO. 18)
   GTA CAG CTG CAG CAG TCA GG 5. 5' TCA GGA GGC GGA GGC TCT GGA GGA GGT GGC AGT CAG  (SEQ ID NO. 19)
   GTC AAC CTG CAG GAG TCT GG Heavy—Anti-sense 1. 5' CGG ACT AGT CTT GGT GGA GGC TGA TGA GAC GGC GAC  (SEQ ID NO. 20)

2. 5' CGG ACT AGT CTT GGT GGG GGC TGA GGA GAC GGC GAC  (SEQ ID NO. 21)

Light (Kappa)—Sense 1. 5' GCA TTA GGC CTC GAG GGC CTC GA(A/T) ATT CAG CTG  (SEQ ID NO. 22)
   AC(G/T) CAG 2. 5' GCA TTA GGC CTC GAG GGC CTC GAC ATC CAG CTG ACC  (SEQ ID NO. 23)
   CAG Light (Kappa)—Anti-sense 5' GAG CCT CCG CCT CCT GAT CCG CCA CCT CCG AAG ACA  (SEQ ID NO. 24)
   GAT GGT GCA GCC ACA GT Light (Lambda)—Sense

5' GCA TTA GGC CTC GAG GGC CTC CCA GCC ATG GCC       (SEQ ID NO. 25)

Light (Lambda)—Anti-sense

5' AGA GCC TCC GCC TCC TGA TCC GCC ACC TCC GGA GGG  (SEQ ID NO. 26)
   GGC AGC CTT

---

What is claimed is:

1. A cross-linker protein comprising
   (a) the antigen-binding site of a first antibody molecule which binds to the constant region of the heavy chain of IgG and
   (b) the antigen-binding site of a second antibody molecule which binds to the secretory component (SC) portion of pIgR, wherein (a) and (b) are independently selected from the group consisting of: a whole antibody, a Fab fragment, an Fv fragment; and a scFv,
   wherein the cross linker protein is constructed by covalently linking (a) and (b).

2. A cross-linker protein comprising:
   (a) the antigen binding domain of a first antibody which binds an antigenic site on the variable region of an autoantibody; and
   (b) the antigen binding domain of a second antibody which binds to the secretory component (SC) portion of pIgR, wherein (a) and (b) are independently selected from the group consisting of: a whole antibody, a Fab fragment, and Fv fragment; and a scFv,
   wherein the cross linker protein is constructed by covalently linking (a) and (b).

3. A pharmaceutical composition comprising the cross-linker protein according to claim 1 in an injectable form.

4. A pharmaceutical composition comprising the cross-linker protein according to claim 2 in an injectable form.

5. The cross-linker protein according to claim 1, wherein
   (a) is an scFv; and
   (b) is an scFv.

6. The cross-linker protein according to claim 1, wherein (a) and (b) are covalently linked by chemical conjugation.

7. The cross-linker protein according to claim 2, wherein
   (a) is an scFv; and
   (b) is an scFv.

8. The cross-linker protein according to claim 2, wherein (a) and (b) are covalently linked by chemical conjugation.

* * * * *